United States Patent [19]

Nakayama et al.

[11] Patent Number: 5,006,468
[45] Date of Patent: Apr. 9, 1991

[54] NOVEL UREASE AND METHOD OF PRODUCING THE SAME

[75] Inventors: Toru Nakayama; Hajime Yoshizumi, both of Osaka; Hiroshi Yamamoto, Kyoto; Kiyoshi Yoshizawa, Saitama, all of Japan

[73] Assignees: Suntory Limited, Osaka; National Tax Administration, Tokyo, both of Japan

[21] Appl. No.: 271,966

[22] Filed: Nov. 16, 1988

[30] Foreign Application Priority Data

Nov. 17, 1987 [JP] Japan .................... 62-289994

[51] Int. Cl.$^5$ ............................... C12N 9/80
[52] U.S. Cl. ........................... 435/228; 435/830
[58] Field of Search .................. 435/227, 830, 228

[56] References Cited
FOREIGN PATENT DOCUMENTS 0079792 5/1983 European Pat. Off. ............ 435/227

OTHER PUBLICATIONS

Suzuki et al., "Urease-producing Species of Intestinal Anaerobes and their Activities", Applied and Environmental Microbiology, 37(3), pp. 379–382, 1979.

Primary Examiner—Douglas W. Robinson
Assistant Examiner—Carol Geckle
Attorney, Agent, or Firm—Cushman, Darby & Cushman

[57] ABSTRACT

A novel urease and a process for producing the same are disclosed. This novel urease has certain properties that are mainly useful for removing urea from alcoholic liquors or other foods and beverages produced by fermentation. These properties include an optimum pH in an acidic pH range, high stability in a considerably high concentration of alcohol such as in an alcoholic liquor, resistance to high temperatures, and highly specific activity to urea.

This urease can be produced by culturing a certain strain belonging to genus Arthrobacter, disrupting the cultured microbial cells and isolating the product.

2 Claims, 4 Drawing Sheets

NOVEL UREASE AND METHOD OF PRODUCING THE SAME

BACKGROUND OF THE INVENTION

The present invention relates to novel urease which is capable of decomposing urea contained in alcoholic beverages and fermentation mashes and causes deterioration of the properties of alcoholic beverages, as well as to a method of producing the same, and relates particularly to a novel form of urease which has an optimum reaction pH value in the acid region and resistance to acidic pH and alcohols and which is produced by a novel microorganism belonging to the genus Arthrobacter, as well as to a method of producing the urease.

Fermented foods and beverages such as Japanese sake, beer, wine, soy source and the like contain urea which is converted from arginine, an amino acid, during fermentation with the aid of arginase which is an enzyme produced by the yeast or molds that take part in the fermentation. Although alcoholic beverages generally contain 2 to 80 ppm of urea, the content of urea in some cases reaches 100 ppm or more when mash is fermented for a long time for the purpose of reducing the lees and increasing the yield.

If an alcoholic beverage contains a large amount of urea, the alcoholic beverage becomes bitter, is discolored and suffers from deterioration of the quality of taste and smell after heat sterilization or long periods of storage.

Ethyl carbamate, a highly carcinogenic compound, is sometimes detected in alcoholic beverages, which is the cause of serious problems [J. Agric. Food Chem., 24, 323 (1976)]. Although the mechanism by which ethyl carbamate is formed has not yet been elucidated, the most plausible hypothesis is that ethyl carbamate is mainly produced from urea or carbamyl phosphate. In other words, it is considered that urea and ethyl alcohol which coexist in alcoholic beverages nonenzymatically react with each other to produce ethyl carbamate.

In order to prevent deterioration of quality, alcoholic beverages are these days required to be sterilized by heating at relatively high temperatures (65° C. or higher) for a certain period (10 minutes or more), and brewages that are stored for a long time as alcoholic beverages have been increasingly used in various fields. Accordingly, a known method of preventing alcoholic beverages from experiencing discoloration and deterioration in flavor due to heating or long-term storage and of preventing the formation of ethyl carbamate is disclosed in Japanese Patent Publication No. 20830/1981. In this method a urease preparation obtained from a certain plant (Jack bean) is added to decompose urea into carbon dioxide and ammonia. In regard to distilled liquors, it is also thought to be effective from the viewpoint of preventing ethylcarbamate formation for the fermented mash that is to be distilled to be first treated with urease for the purpose of decomposing any urea in the mash, because the formation of ethylcarbamate is accelerated at the high temperatures that subsist during distillation.

No urease having suitable characteristics for this purpose is, however, known at present. In other words, it is known that the optimum pH of many kinds of urease for enzyme reactions is generally neutral or weak alkaline (see Japanese Patent Publication No. 55119/1985 and Japanese Patent Public Disclosure Nos. 17987/1984 and 257183/1986), and that these ureases exhibit very little activity and are considerably unstable at an acidic pH or at a high concentration of alcohol as when present in alcoholic liquors [Jack bean urease, Eur. J. Biochem. 73, 185 (1977), Bacillus pasteurri urease, The Enzymes 3rd ed. 4, 1 (1971)]. It is therefore an object of the present invention to provide urease having characteristics that allow the urea to be efficiently decomposed in fermented foods and beverages (particularly alcoholic liquors), that is, to provide a urease having an acidic optimum pH value for reaction and a desirable degree of resistance to acidic pH and alcohol.

Although it is known that *Arthrobacter oxydans*, which is a bacterium belonging to the same genus as that of the strain of the present invention [Arch. Microbiol., 139, 355 (1984)], produces a urease, it has a neutral optimum pH for reaction and thus fails to meet the objectives of the present invention. This urease is thus the same as many kinds of urease derived from other bacteria. A urease produced by *Lactobacillus fermentum*, which is an anaerobic bacterium, is known to have an optimum pH value for reaction in an acid region [Appl. Environ. Microbiol., 37, 379 (1979)]. The urease produced by this strain, however, has the disadvantage that the urease strongly binds to the membrane of the bacterium, and thus cannot be easily purified, rendering it unsatisfactory.

SUMMARY OF THE INVENTION

As a result of extensive screening of ureases to find one having the characteristic of decomposing urea in alcoholic liquors at an acidic pH and a high concentration of alcohol, the inventors found that a strain belonging to the genus Arthrobacter produces urease having a characteristic satisfying with the needs of the present invention. This strain is cultured in a liquid or solid medium to produce a urease which is then purified so that it can be used as an enzyme agent capable of efficiently removing urea from alcoholic liquors. In summary, the present invention provides a novel urease and a method of producing the enzyme concerned.

The inventors of this invention searched for microorganisms which can produce a urease exhibiting a desired activity at an acidic pH, and found microorganisms which can produce the desired acid urease which were isolated from the solid in pasture land at Hidaka-machi, Saryu-gun, Hokkaido. The mycological characteristics of the microorganisms that are useful in the present invention are described below.

A. MORPHOLOGY (1) The cells are pleomorphic.

Cells which are grown in a medium for at least 24 hours are short rods having a width of about 0.8 $\mu$m and a length of about 1.0 $\mu$m. When these cells are inoculated in a fresh L medium (comprising 1% polypeptone, 0.5% yeast extract, 0.5% NaCl and 0.1% glucose; pH 7.0) and then shaking-cultured at 30° C. for about 3 hours, rods having a width of about 0.8 $\mu$m and a length of about 2.5 $\mu$m are formed, as well as V-shape cells. On continuing the culture, the cells begin to gradually divide after about 9 hours of cultivation to form the short rods similar to the original sphere-like cells after cultivation for about 24 hours.

(2) No spore is formed.

(3) The microorganisms have mobility and polar flagella.

(4) The microorganisms are gram-negative when cultured in an L medium containing 1.5% of agar at 30° C. for 24 hours, while they are gram-positive when the gram-reactivity is determined in terms of alanine aminopeptidase activity with respect to microorganisms cultured under the same conditions as those described above.

B. CULTURAL GROWTH CONDITIONS IN THE FOLLOWING MEDIA (1) Meat extract liquid medium The microorganisms are light yellow, turbidity is observed throughout the medium, and precipitate is observed at the bottom.

(2) Meat extract-agar plate medium

The microorganisms are vigorously grown and have a light yellow color. Each colony has a diameter of about 3 to 5 mm, a smooth and glossy surface, and an intact edge.

(3) Meat extract-agar slant medium

The microorganisms show the same growth profile as with the meat extract-agar plate medium in (2). They are grown in a distributed manner.

(4) Meat extract-gelatin stab medium

The gelatin is liquefied.

(5) Litmus milk

The color of the litmus milk changes to light brown, but neither coagulation nor liquefaction is observed.

C. PHYSIOLOGICAL CHARACTERISTICS

| | |
|---|---|
| (1) Reduction of nitrate | + |
| (2) Hydrolysis of starch | − |
| (3) Decomposition of casein | − |
| (4) Resistance to 5% NaCl | + |
| (5) Resistance to 10% NaCl | + |
| (6) Production of catalase | + |
| (7) Production of oxidase | − |
| (8) Production of urease | + |
| (9) Production of extracellular DNase | + |
| (10) Ability to liquefy gelatin | + |
| (11) Behavior with respect to oxyen | aerobic |
| (12) Growth temperature range | 10–36° C. |
| Optimal growth temperature, 31° C. | |
| (13) Growth pH range | 6.0–10.0 |
| Optimal pH, 7.8 | |

D. PRODUCTION OF ACID AND GAS FROM CARBOHYDRATES

| | Production of acid | Production of gas |
|---|---|---|
| (1) L-Arabinose | − | − |
| (2) D-Xylose | − | − |
| (3) D-Glucose | − | − |
| (4) D-Mannose | − | − |
| (5) D-Fructose | − | − |
| (6) D-Galactose | − | − |
| (7) Maltose | − | − |
| (8) Saccharose | − | − |
| (9) Lactose | − | − |
| (10) Trehalose | − | − |
| (11) Soluble starch | − | − |
| (12) D-Sorbitol | − | − |
| (13) D-Mannitol | − | − |
| (14) Inositol | − | − |
| (15) Glycerin | − | − |

E. UTILIZATION OF CARBON SOURCE

| | |
|---|---|
| (1) 4-Aminobutyric acid | ± |
| (2) p-Hydroxybenzoic acid | − |
| (3) L-Leucine | ± |
| (4) L-Asparagine | + |
| (5) L-Arginine | + |
| (6) L-Histidine | − |
| (7) D-Xylose | + |
| (8) D-Ribose | + |
| (9) D-Arabinose | + |
| (10) L-Rhamnose | + |
| (11) Inositol | ± |
| (12) Malonic acid | ± |
| (13) Citric acid | − |
| (14) Glucose | + |

The utilization of each of these carbon sources was determined in accordance with the method described in Zentralblatt für Bakteriologie, vol. I, pp 357–375, 1980.

F. UTILIZATION OF ORGANIC ACID

| | |
|---|---|
| (1) Citric acid | − |
| (2) Formic acid | + |
| (3) Malonic acid | − |
| (4) Glutaric acid | ± |
| (5) Adipic acid | − |
| (6) Pimelic acid | − |
| (7) Uric acid | − |
| (8) Benzoic acid | − |
| (9) Propionic acid | + |

The utilization of each of these organic acids was determined in accordance with the method described in The Journal of General and Applied Microbiology, vol. 18, pp 399–416, 1972.

G. GC CONTENT OF DNA

The GC content of DNA was 65.2%. The determination was performed in accordance with the method described in FEMS Microbiology Letters, 25, 125–128 (1984).

H. ANALYSIS OF ISOPRENOID QUINONES

The isoprenoid quinone comprises a major amount of menaquinone of MK-9 ($H_2$). Isoprenoid quinone was analyzed by the method described in "Ubiquinone and Menaquinone" by Yuzo Yamada and Hiroshi Kuraishi, "Experimental Method for Chemotaxonomy of Microorganisms" edited by Kazuo Komagata, pp 143–155, 1982, issued by the Gakkai Shuppan Center (Tokyo).

I. COMPOSITION OF CELLULAR FATTY ACID

The cellular fatty acids comprise branched (iso, anteiso) fatty acids as principal components and substantially no unsaturated fatty acid. The composition ratios (%) of the fatty acids are shown in Table 1.

TABLE 1

| Anteiso fatty acids | | Iso fatty acids | | | | Straight chain unsaturated fatty acids | | | | |
|---|---|---|---|---|---|---|---|---|---|---|
| a-15 | a-17 | i-14 | i-15 | i-16 | i-17 | n-14 | n-15 | n-16 | n-17 | n-18 |
| 50 | 14 | 2 | 5 | 7 | 2 | 3 | 2 | 14 | — | 1 |

The composition was determined by the method described in the International Journal of Systematic Bacteriology, 33, 188–200 (1983).

J. PEPTIDOGLYCAN TYPE OF CELL WALLS

The cell wall peptidoglycan of the microorganisms contains lysine as the diamino acid and the walls contain the peptidoglycan of Lys-Thr-Ala-Ala type.

The identification of the diamino acid in the peptidoglycan of the cell walls and the determination of the molar ratios of the constituent amino acids were performed with an amino acid autoanalyzer (HITACHI AMINO ACID ANALYZER 835-50) after the cell walls had been purified and hydrolyzed in accordance with the method described in The Journal of General and Applied Microbiology, 16, 103-113 (1970).

The cells were disrupted using an ultrasonic oscillator.

It is considered from the molar ratio of the amino acid constituents of the cell walls of the strain of the present invention (Lysine:glutamic acid:alanine:threonine=1:1:4:1) that the peptidoglycan type is Lys-Thr-Ala-Ala or Lys-Ala-Thr-Ala, with reference to Journal of Bacteriology, 113, 8-17 (1973).

The latter teaches that the oligopeptides derived from partial acid hydrolysates of a peptidoglycan of the Lys-Thr-Ala-Ala type contain Thr-$\epsilon$-Lys, while the oligopeptides derived from a peptidoglycan of the Lys-Ala-Thr-Ala type contain Ala-$\epsilon$-Lys.

The cell wall peptidoglycan of the microorganisms was thus partially hydrolyzed with 4N-HCl for 30 minutes or 1 hour at 100° C. to give oligopeptides. The resulting oligopeptides and dipeptides i.e. Ala-$\epsilon$-Lys and Thr-$\epsilon$-Lys which had been synthesized were analyzed using an amino acid autoanalyzer (HITACHI AMINO ACID ANALYZER 835-50). With respect to the partial acid hydrolysates of the cell wall peptidoglycan of the microorganisms of the present invention, a peak was detected at a retention time equal to that of Thr-$\epsilon$-Lys, while no peak was detected at a retention time equal to that of Ala-$\epsilon$-Lys.

When the mixture of the partial acid hydrolysates of the cell wall peptidoglycan of the microorganisms and the synthesized dipeptide Thr-$\epsilon$-Lys were analyzed with the amino acid autoanalyzer, the area of the peak equal to that of Thr-$\epsilon$-Lys was greater. It was therefore confirmed that the partial acid hydrolysates of the peptidoglycan contain Thr-$\epsilon$-Lys.

As a result, it is clear that the strain of the present invention has the Lys-Thr-Ala-Ala type of peptidoglycan.

K. DNA-DNA HYBRIDIZATION TEST

DNA-DNA homologies (%) between *Arthrobacter citreus* IAM12341 of this invention which has an Lys-Thr-Ala-Ala type of cell wall peptidoglycan and *Arthrobacter ureafaciens* IAM1658 which has an Lys-Ala-Thr-Ala type of cell wall peptidoglycan are shown in Table 2.

TABLE 2

| Non-labelled DNA | Labelled DNA | | |
|---|---|---|---|
| | SAM0752 | Arthrobacter citreus IAM12341 | Arthrobacter ureafaciens IAM1658 |
| SAM0752 | 100 | 27 | 22 |
| Arthrobacter citreus IAM12341 | 27 | 100 | 10 |
| Arthrobacter ureafaciens IAM1658 | 18 | 12 | 100 |

The DNA-DNA hybridization tests were carried out by the method described in International Journal of Systematic Bacteriology, 31, 131-138 (1981).

When the taxonomic class of the strain SAM0752 of the present invention was determined on the basis of the above-mentioned mycological properties thereof in accordance with Bergey's Manual of Systematic Bacteriology, Vol. 2, it was found that this strain belongs to the coryneform group because it belongs to Gram-positive aerobic bacteria, is pleomorphic, forms no spores, and exhibits a GC content of DNA of 65.2%.

Furthermore, this strain contains lysine in a cell wall peptidoglycan, has MK-9 ($H_2$) as a major isoprenoid quinone, and the major components of the cellular fatty acids were branched fatty acids mainly comprising 12-methyltetradecanoic acid (a-15) and 14-methylhexadecanoic acid (a-17). Thus, it is thought that this strain belongs to the genus Arthrobacter according to The Journal of General and Applied Microbiology, 18, 417-431 (1972) and 22, 203-214 (1976) and International Journal of Systematic Bacteriology, 33, 188-200 (1983).

As a result of more precise investigations, it was found that the strain of the present invention belongs to the same group as *Arthrobacter citreus* because the cell wall peptidoglycan of this strain is of the Lys-Thr-Ala-Ala type. Refer to Archives of Microbiology, 12, 289-295 (1979) and Journal of Bacteriology, 113, 8-17 (1973). Only *Arthrobacter citreus* is known at present as a species having an Lys-Thr-Ala-Ala type of peptidoglycan belonging to the genus Arthrobacter.

The differences in physiological properties between the strain of the present invention and *Arthrobacter citreus* IAM12341 (standard strain) are shown in Table 3. As shown in Table 3, the strain of the present invention differs from the latter in the utilization of citric acid and malonic acid, the resistance to 10% NaCl, the ability to produce urease and utilization of arginine and xylose.

The results of a DNA-DNA hybridization test between the strain of this invention and *Arthrobacter citreus* IAM12341 or *Arthrobacter ureafaciens* IAM1658 (standard strain) revealed that this strain showed 30% or less homology with respect to each of these two strains and can thus be thought to be different from these two species.

On the basis of the above description, the inventors concluded that the strain SAM0752 should be classified as a new species of the genus Arthrobacter and it was named as *Arthrobacter mobilis*.

This *Arthrobacter mobilis* SAM0752 was deposited as Deposit No. 9658 (FERM P-9658) and converted on Oct. 27, 1988 to an international deposition under the Budapest Treaty as (FERM BP-2127) in the Fermentation Research Institute Japan.

TABLE 3

| | SAM0752 | Arthrobacter citreus IAM12341 |
|---|---|---|
| Utilization of citric acid | − | + |
| Utilization of malonic acid | − | + |

TABLE 3-continued

|  | SAM0752 | *Arthrobacter citreus* IAM12341 |
|---|---|---|
| Resistance to 10% NaCl | + | − |
| Ability to produce urease | + | − |
| Fermentability of arginine | + | − |
| Fermentability of xylose | + | − |

The culture of the strain of the present invention can be performed through a usual culture method such as a liquid culture method, for instance, aerobic agitation or shaking, or a stationary culture; or a solid culture method.

Culture medium ingredients which are useful in the present invention include glucose, starch, sucrose and lactose, which may be used as carbon source; peptone, yeast extract, urea or ammonium sulfate as nitrogen source; potassium phosphate, magnesium sulfate or calcium chloride as inorganic salt; and, if required, a minor metal ion such as $Zn^{++}$, $Cu^{++}$, $Fe^{++}$ or $Ni^{++}$ and a vitamin such as biotin or thiamin. Although the temperature of the cultivation is not critical so long as microorganisms can be grown, 30° C. is preferable. The culture is performed for 15 to 72 hours through any one of the culture methods described above.

In order to isolate the urease from the thus-obtained cultured substance, the cultured substance is first separated into broth and cell fractions by centrifugation or filtration. The cells are then disrupted by a glass beads methods, a French press method, an ultrasonic method or an autolysis methods. These methods can be used alone or in a combination of two or more thereof. Then, the residual cells are removed to obtain a crude enzyme sample.

If a concentrated sample or a purified sample is necessary, it can be obtained by a conventional purification method such as ultrafiltration, dialysis, salting out, solvent precipitation, ion-exchange chromatography, gel filtration chromatography, adsorption chromatography or isoelectric precipitation singly or in a combination of two or more of these methods.

The enzymological properties of the purified urease produced by the strain of the present invention are summarized below.

(1) THERMAL STABILITY

Figure 1:
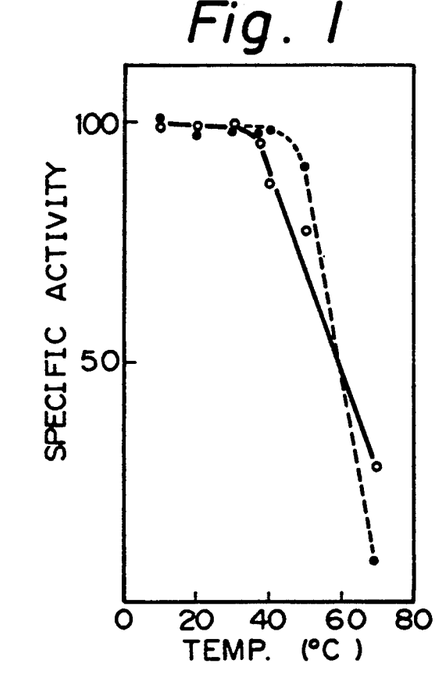
FIG. 1 is a graph showing the thermal stability of purified urease.

The enzyme was treated at a temperature of from 10° to 70° C. for 15 minutes in a 0.1M acetic acid buffer (pH 4.5) or a 0.1M acetic acid buffer (pH 4.5) containing 20% (v/v) of ethanol. The results of measuring the residual activity of the enzyme treated at different temperatures revealed that the enzyme is substantially stable at 40° C. and 50° C. in buffers containing or not containing ethanol (FIG. 1).

(2) OPTIMUM TEMPERATURE

Figure 2:
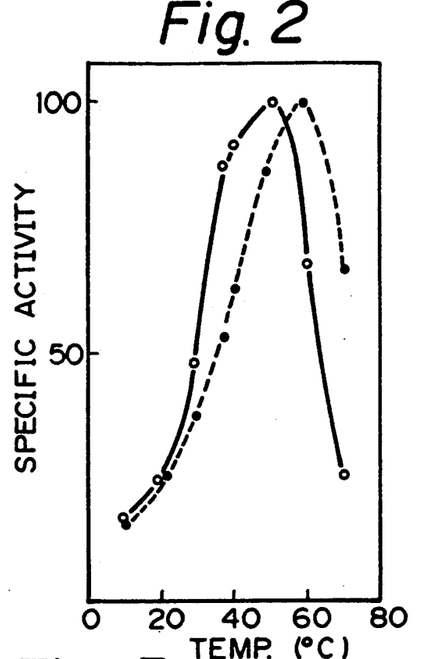
FIG. 2 is a graph showing the optimum temperature of the urease.

The optimum temperature for the urease activity in each of the buffers used in (1) was measured at approximately 50° C. in the buffer containing no ethanol and at 60° C. in the buffer containing ethanol (FIG. 2).

(3) pH STABILITY

Figure 3:
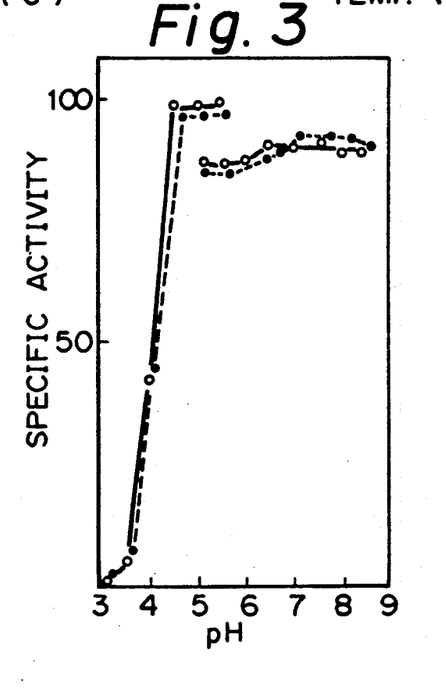
FIG. 3 is a graph showing the pH stability of the urease.
Figure 4:
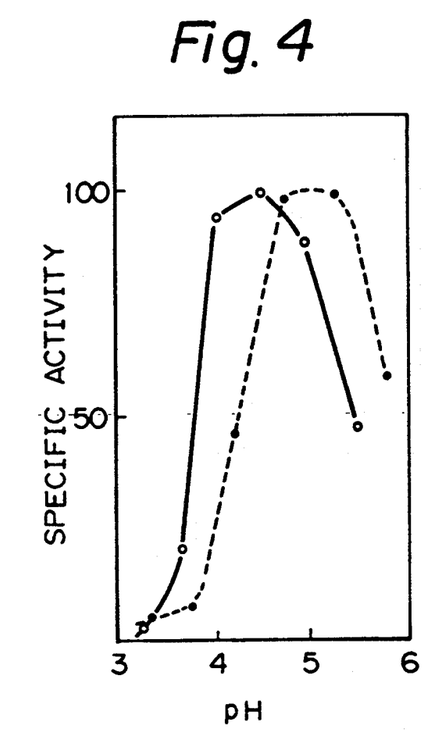
FIG. 4 is a graph showing the optimum pH value of the urease.

After the enzyme was treated with 0.1M acetic acid buffer (pH 3.2 to 5.5) and 0.1M phosphate buffer (pH 5.0 to 8.5) at 4° C. for 16 hours. Each of the buffers was used in the absence of or in the presence of 20% of ethanol, respectively, and, the residual activity was measured. The results showed the enzyme to be stable at a pH of more than 4.5 under both of these conditions (FIG. 3). (4) OPTIMUM pH The optimum pH for urease reaction in a 0.1M acetic acid buffer was approximately 4.2 in the case where no ethanol was added, and about 5.0 in case 20% of ethanol was added (FIG. 4).

(5) RESISTANCE TO ETHANOL

Figure 5:
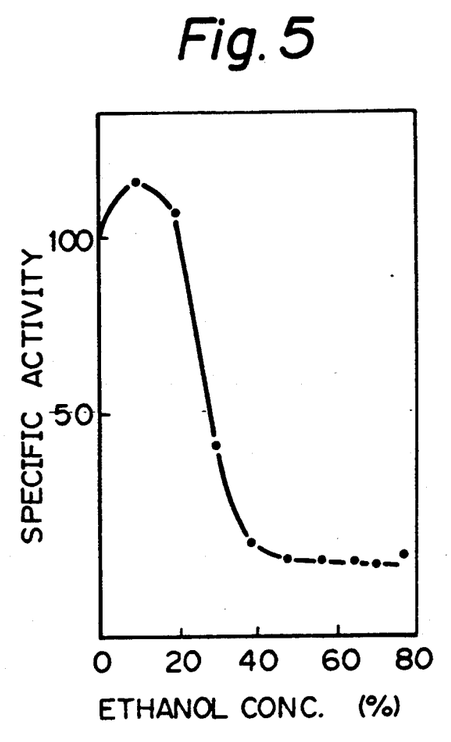
FIG. 5 is a graph showing the influence of the concentration of added ethanol on the enzyme activity.

The enzyme activity was measured in each of 0.1M acetic acid buffers (pH 4.5) containing 0 to 80% (v/v) ethanol. The result revealed that the enzyme remained stable in the buffer containing up to about 25% of ethanol and that the activity tended to be high in the presence of ethanol (FIG. 5).

(6) KM VALUE FOR UREA

The Km value of the enzyme for urea in a 0.1M acetic acid buffer (pH 4.5) at 37° C. was about 3.6 mM in the case where no ethanol was added and about 3.7 mM in the case where 20% ethanol was added.

(7) MOLECULAR WEIGHT

The result of determination through gel filtration using high performance liquid chromatography showed, the molecular weight of this enzyme to be about 240,000. A TSK 3000 SW XL analytical column (Toso Co., Ltd.) was used as a gel filtration carrier. The molecular weight was calculated from the retention time on the basis of those of various standard proteins (product of Oriental Yeast Co., Ltd.) under conditions wherein 20 mM Tris-HCl buffer (pH 7.5) containing 0.7M NaCl was used as eluent at a flow rate of 0.5 ml/min.

The subunit molecular weight of the enzyme of the invention was determined to be 67,000 through SDS polyacrylamide gel electrophoresis (SDS-PAGE). The molecular weight was determined from the mobility relative to those of various standard proteins which were obtained by using a Phast System electrophoretic analyzer with use of Phase Gel Gradient 8–25 manufactured by Pharmacia Co., Ltd. It is believed that the enzyme of the invention is a tetramer.

(8) ISOELECTRIC POINT

The pI of the enzyme of the invention was about 6.8 when determined by an isoelectric focusing method. This value was determined with a Phast System electrophoretic analyzer using Phast Gel IEF 3-9 manufactured by Pharmacia Co., Ltd. from the mobility relative to those of various standard proteins sold by BDH Chemical Co., Ltd.

(9) SUBSTRATE SPECIFICITY

The results of enzyme reaction with compounds analogous to urea at a substrate concentration of 100 mM revealed that the enzyme of this invention had a very high specificity for urea (Table 4).

(10) INHIBITOR

The activities of the enzyme were inhibited by certain metal ions such as $Hg^{++}$, $Ag^+$ and $Cu^{++}$ (Table 5).

TABLE 4

| Substrate (100 mM) | Relative activity (%) |
|---|---|
| Urea | 100 |
| N-Methylurea | 1.7* |
| Acetamide | 0.0 |
| Phenylurea | 0.0 |

TABLE 4-continued

| Substrate (100 mM) | Relative activity (%) |
| --- | --- |
| Guanidine HCl | 0.0 |
| Thiourea | 0.0 |
| Semicarbazide | 1.0* |
| Hydroxyurea | 0.0 |
| Ethylurethane | 0.0 |
| Carbamyl phosphate | 0.0 |

TABLE 5

| Metal Salt (1 mM) | Relative activity (%) |
| --- | --- |
| No addition | 100 |
| $CaCl_2$ | 81 |
| $MnCl_2$ | 102 |
| $BaCl_2$ | 59 |
| $NiCl_2$ | 61 |
| $CoCl_2$ | 100 |
| $CuCl_2$ | 3 |
| $PbCl_2$ | 115 |
| $CdCl_2$ | 125 |
| $HgCl_2$ | 3 |
| $ZnCl_2$ | 63 |
| $AgNO_3$ | 0 |
| KCl | 100 |
| NaCl | 95 |

The activity was determined by measuring the amount of ammonia produced by decomposition of urea during the enzyme reaction per unit of time. In particular, 0.025 ml of an enzyme solution was added to a reaction solution containing 0.2 ml of a 0.1M acetic acid buffer (pH 4.5) and 0.025 ml of a 0.1M urea solution, followed by incubation at 37° C. for a given time (10 to 20 minutes). The reaction was terminated by adding 0.025 ml of a 33% trichloroacetic acid solution. One ml of the reaction solution was added to 1 ml of a coloring solution which had been prepared by mixing 10 ml of a 0.3M phosphate buffer (pH 7.5), 0.56 ml of 25 mg/ml o-phthalaldehyde in ethanol, and 0.56 ml of 5 mg/ml 2-mercaptoethanol in ethanol. After allowing the thus-obtained mixture to stand for 45 minutes at room temperature, the increase in absorbance at a wavelength of 410 nm was measured. The enzyme activity was then calculated from a calibration curve which was formed using predetermined amounts of ammonium chloride as a reference substance. This method was based on the method by Heini et al. [Eur. J. Biochem., 162, 541 (1987)]. The activity unit of the enzyme was defined as the amount of ammonia produced in terms of $\mu$ mol/min.

It is therefore thought from the aforementioned various enzymological properties that the urease produced by the novel microorganisms of the present invention is novel urease.

BRIEF DESCRIPTION OF THE DRAWINGS

In each of FIGS. 1 to 4, the solid line shows a case where no ethanol was added, and the dashed line shows a case where ethanol was added.

DETAILED DESCRIPTION OF THE INVENTION

The present invention is described in detail below with reference to examples.

EXAMPLE 1

Several portions of a medium (200 ml) composed of 1.0% of polypeptone, 0.5% of yeast extract and 0.5% of NaCl were placed in 500 ml-Meyer flasks, and one platinum loop of the strain of this invention was inoculated and shaking cultured at 28° C. for 24 hours. The cultured substances were used as a seed culture for a main culture of the type mentioned below.

30 l of a medium at pH 7.2 which comprised 1.0% of glucose, 0.5% of polypeptone, 0.05% of meat extract, 0.001% of yeast extract, 0.2% of $KH_2PO_4$ and 0.5% of NaCl was placed in a 50-l vessel for aerobic agitating culture which was then vapor-sterilized for 30 minutes. The above-described seed culture were inoculated in the culture vessel, followed by cultivation at 0.8 vvm and 30° C. for 24 hours. After the cultivation, the cultured substance was centrifuged to obtain cells which were then washed with a 10 mM phosphate buffer (pH 7.4) to obtain cells having a wet weight of 80 g. The thus-obtained cells suspended in the phosphate buffer was disrupted by using Dynomill (produced by Willy A. Bachofen Co., Ltd., with glass beads having a diameter of 0.1 mm, at a flow rate of 60 ml/min). The solution obtained by disruption of the cells had 13,000 units of enzyme activity. The specific activity was 1.0 unit per mg of protein.

1.6 l of the disrupted cell suspension was loaded on an ion-exchange resin FP DA 13 column (produced by Mitsubishi Chemical Co., Ltd., 6×10 cm) which was previously equilibrated by a 10 mM phosphate buffer (pH 7.4). Elution was carried out by using 2.0 l of phosphate buffer with a linear gradient from 0M KCl to 0.6M KCl to obtain 600 ml (9,600 units) of active urease fractions. The specific activity of the thus-obtained active fractions was 5.0 units per mg of proteins.

The thus-obtained active fractions were then purified by hydrophobic chromatography. The active fractions which were previously adjusted to give a KCl concentration of 2.5M were loaded on a Butyl Toyopearl 650C column (produced by Toso Co., Ltd., 3×30 cm) which was previously equilibrated by a 0.1M phosphate buffer (pH 7.0) containing 2.5M of KCl. The enzyme active fractions were eluted while the concentration of KCl was linearly reduced by using distilled water as a diluent. The total activity of the thus-obtained active fractions was 4,800 units, and the specific activity thereof was 40 units per mg of protein.

EXAMPLE 2

The enzyme (60 mg of protein) obtained in Example 1 was dialyzed against a 20 mM Tris-HCl buffer solution (pH 7.5) to obtain a dialyzed enzyme sample. This sample was then purified by using ion-exchange chromatography and gel filtration chromatography as follows. The dialyzed sample was loaded on DEAE Toyopearl 650S (produced by Toso Co., Ltd.) which was equilibrated by the same buffer as that used in dialysis so that enzyme active fractions were eluted with the 20 mM Tris-HCl buffer while the concentration of NaCl was linearly increased.

The total activity of the thus-obtained active fractions was 1,200 units, and the specific activity thereof was 180 unit per mg of protein.

The thus-obtained active fractions were concentrated by precipitation using 70% saturated ammonium sulfate, centrifuged and then dissolved in a 20 mM Tris-HCl buffer containing 0.7M of NaCl. The enzyme active fractions were collected by elution from a TSK G300SW×L column (produced by Toso Co., Ltd.) equilibrated with the buffer used in the dissolution at a flow rate of 0.5 ml/min. The total activity of the enzyme purified by the above-described method was 580 units, and the specific activity thereof was 970 units per mg of protein.

EXAMPLE 3

The urease sample obtained in Example 1 was used in removal of urea by decomposition in Japanese sake (in this example, containing 19% ethanol at pH 4.0).

Figure 6:
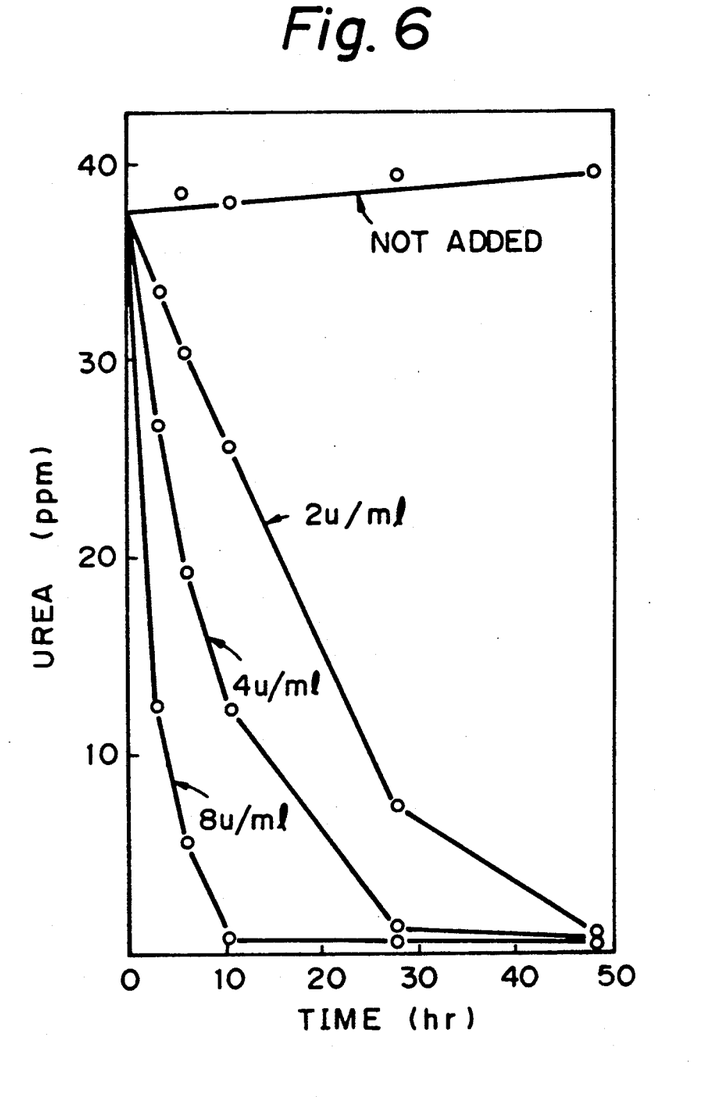
FIG. 6 is a graph showing the change in amount of residual urea at 10° C. with the passage of time when an urease sample is added to Japanese sake.

The urease enzyme sample was added to the Japanese sake in such a manner that the final activity was 0 to 8 units/ml, followed by incubation at a low temperature (10° C.). 0.1 ml aliquots of the Japanese sake treated with urease as above were withdrawn at appropriate time intervals, and 1.8 μl of 33% of trichloroacetic acid was added to each to terminate the reaction. After the Japanese sake had been neutralized with 5 μl of 1.0N sodium hydroxide, the content of the residual urea was measured by using a urea-ammonia assay kit F (product of Boehringer Mannheim Yamanouchi Co., Ltd.). The results obtained are shown in FIG. 6. As shown in this figure, it was confirmed that the used amount of enzyme in this example can remove urea by decomposition to a level below the limit (1 ppm) of measurement within 48 hours.

When sense tests of the changes that occurred in the taste and smell of the Japanese sake used due to addition of urease were performed, no offensive taste or odor was observed.

EXAMPLE 4

Figure 7:
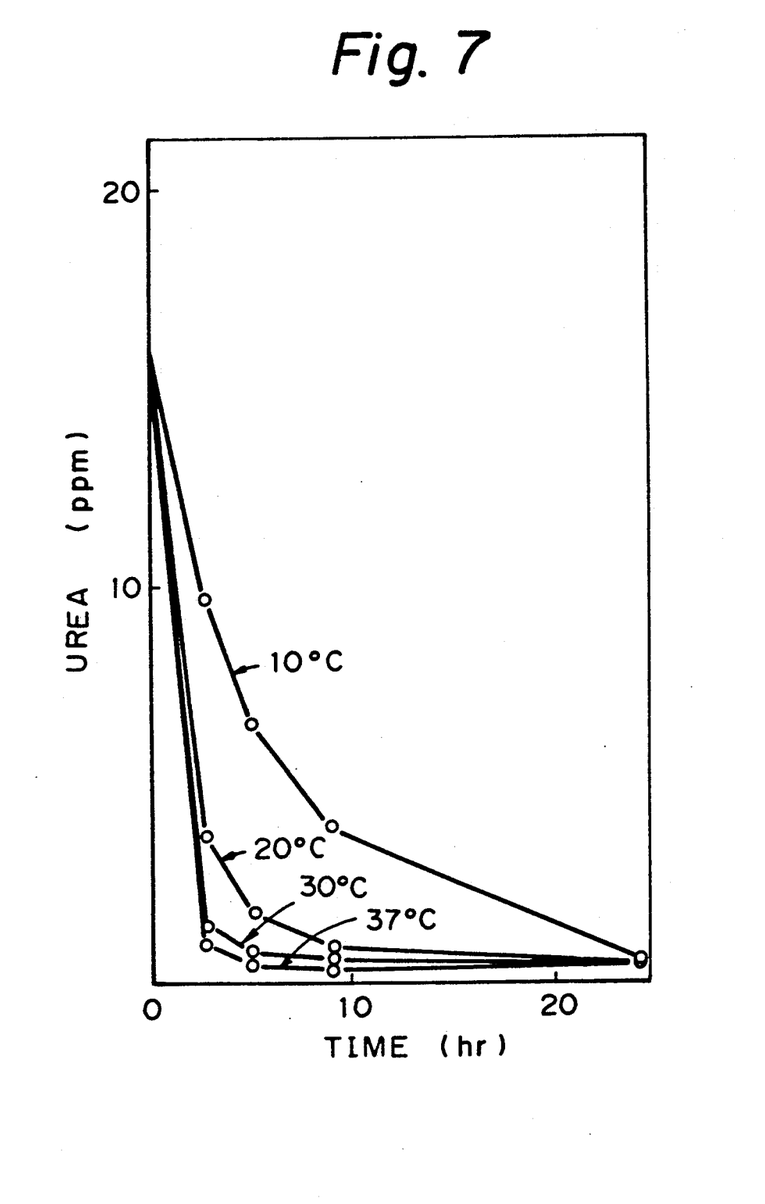
FIG. 7 is a graph showing the effect of temperature on the decomposition of urea by urease.

Tests were made to determine the temperature dependence of decomposition of the urea contained in Japanese sake brought about by the urease sample. The Japanese sake used contained 19% ethanol and had a pH value of 4.1, and reaction was effected by using a final amount of 4 units/ml of enzyme. The amount of residual urea was quantified by the same method as that used in Example 3. The results obtained are shown in FIG. 7. As shown in this figure, it was observed that the amount of urea is rapidly reduced by decomposition to a level below the limit of measurement within a medium temperature range of 20° to 37° C.

EXAMPLE 5

The effect of the urease of the present invention was examined with respect to the removal of urea contained in fermentation mash by using mash at the final state of fermentation of Japanese sake (containing 19% ethanol and 35 ppm of urea and having a pH value of 4.1) and mash at the final stage of fermentation of Bourbon whisky (containing 8.5% of ethanol and 45 ppm of urea and having a pH value of 4.2). The conditions for urease treatment and the method of measuring the residual urea were the same as those employed in Example 3. It was confirmed that the amount of the urea was reduced to a level below the limit of measurement within 48 hours.

EXAMPLE 6

The decomposition of the urea contained in Japanese sake was tested by adding cells of the strain of the present invention to the Japanese sake. The cells of the strain used was obtained as follows. One platinum loop of the strain was inoculated in the medium used for preparing the seed culture in Example 1, and cultivated at 28° C. for 24 hours. After centrifugation, collected cells were washed with distilled water three times and concentrated to 10 times the original concentration so as to be suspended in the distilled water. The Japanese sake used was the same as that used in Example 3. 0.1 ml of the cell suspension was added to 10 ml of the Japanese sake, and the thus-obtained mixture was then allowed to stand at 10° C. for 48 hours. As a result, the amount of urea in the Japanese sake was reduced from an initial level of 31 ppm to a level below the limit (1 ppm) of measurement.

EXAMPLE 7

1,000 chitosan beads BCW-3013 (produced by Fuji Spinning Co., Ltd.) were added to 50 ml of an aqueous solution containing 5.0 mg (550 units) of the purified urease sample obtained in Example 2, followed by agitation at room temperature for 2 hours. 5 ml of an aqueous solution of 5% genipin was added to the obtained mixture, followed by gentle agitation for 18 hours. The chitosan beads were collected and washed twice with 10 ml of distilled water to obtain urease-immobilized beads. The urease enzyme activity of the thus-obtained beads was 500 units per 1,000 beads. After 50 beads of the urease-immobilized beads obtained had been added to 10 ml of the Japanese sake used in Example 3, followed by reaction at 30° C. for 10 hours under agitation, the amount of the residual urea was measured. The results showed that the urea had decomposed to a level below the limit of measurement.

It was confirmed that the urea contained in brewages such as Japanese sake and the like is decomposed to a level below the limit of measurement by adding to brewages the urease sample of the present invention or the cells of the strain of the invention which produces the same urease. In regard to fermentation mash for Japanese sake and fermentation mash for distilled liquors such as Bourbon whisky and the like, addition of the urease sample of the present invention to such a mash at the final stage of fermentation exhibited the same effect as that described above.

The object of the present invention can also be achieved. If various support media in which the urease sample of the present invention is immobilized using a known enzyme immobilization technique are used as urease enzyme agents.

We claim:

1. A substantially pure urease capable of being produced by a microorganism of the strain Arthrobacter mobilis SAM0752 having the following pyhsical and chemical properties:
   (1) function:
      catalyzing hydrolysis of 1 mole of urea to produce 2 moles of ammonia and 1 mole of carbon dioxide at an optimum pH in the range of 4.2 to 5.0 and an optimum temperature in the range of 50°–60° C.;

(2) pH stability:
  stable between pH 4.5 and 8.5 in treatment at 4° C. for 16 hours;
(3) temperature stability:
  stable up to 50° C. in treatment at pH 4.5 for 15 minutes;
(4) substrate specificity:
  having an extremely high degree of specificity to urea;
(5) inhibitor:
  $Hg^{++}$, $Ag^+$ or $Cu^{++}$ ions;
(6) Km value:
  in the range of 3.6 to 3.7 mM (pH 4.5, 0.1M acetic acid buffer);
(7) molecular weight:
  about 240,000 (measured by a gel filtration method; and
(8) isoelectric point:
  at a pI value of between 6.5 and 7.0.

2. A method of producing an urease characterized by the physical and chemical properties described below comprising culturing microorganisms of the strain *Arthrobacter mobilis* SAM0752, which produces a recoverable amount of the said urease and recovering said urease, the physical and chemical properties are, (1) function:
  catalyzing hydrolysis of 1 mole of urea to produce 2 moles of ammonia and 1 mole of carbon dioxide at an optimum pH in the range of 4.2 to 5.0 and an optimum temperature in the range of 50°-60° C.;
(2) pH stability:
  stable between pH 4.5 and 8.5 in treatment at 4° C. for 16 hours;
(3) temperature stability:
  stable up to 50° C. in treatment at pH 4.5 for 15 minutes;
(4) substrate specificity:
  having an extremely high degree of specificity to urea;
(5) inhibitor:
  $Hg^{++}$, $Ag^+$ or $Cu^{++}$ ions;
(6) Km value:
  in the range of 3.6 to 3.7 mM (pH 4.5, 0.1M acetic acid buffer);
(7) molecular weight:
  about 240,000 (measured by a gel filtration method); and
(8) isoelectric point:
  at a pI value of between 6.5 and 7.0.

* * * * *